United States Patent [19]

Hucul

[11] Patent Number: 5,336,822
[45] Date of Patent: Aug. 9, 1994

[54] PROCESS FOR THE PRODUCTION OF STYRENE

[75] Inventor: Dennis A. Hucul, Midland, Mich.

[73] Assignee: The Dow Chemical Company, Midland, Mich.

[21] Appl. No.: 75,962

[22] Filed: Jun. 14, 1993

Related U.S. Application Data

[63] Continuation-in-part of Ser. No. 827,131, Jan. 28, 1992, abandoned.

[51] Int. Cl.$^5$ .......................... C07C 5/367; C07C 5/48
[52] U.S. Cl. ................................... 585/444; 585/435; 585/658
[58] Field of Search ................ 585/444, 435, 654, 658

[56] References Cited

U.S. PATENT DOCUMENTS

| | | | |
|---|---|---|---|
| 3,094,565 | 6/1963 | Bethell et al. | 260/604 |
| 3,258,432 | 6/1966 | Gasson et al. | 252/461 |
| 3,308,183 | 3/1967 | Bajars | 260/680 |
| 3,309,325 | 3/1967 | Gasson et al. | 252/461 |
| 3,328,478 | 6/1967 | Barclay et al. | 260/680 |
| 3,346,513 | 10/1967 | Hadley | 252/461 |
| 3,370,103 | 2/1968 | Callahan et al. | 260/680 |
| 4,036,901 | 7/1977 | Kawakami et al. | 260/669 R |
| 4,165,441 | 8/1979 | Okano et al. | 585/444 |

OTHER PUBLICATIONS

CA 93:149958w (1980) Mitsubishi Chem. Ind. Co., Ltd. (abstract only of Japan Kokai Tokkyo Koho 80 57,522).
CA 92:23138q (1980) Kageyama et al. (abstract only of Japan Kokai Tokkyo Koho 79,119,422).
CA 90:138404z (1979) Okano et al. (abstract only of Japan Kokai Tokkyo Koho 78,144,534).
CA 94:65292g (1981) Mitsubishi Chem. Ind. Co., Ltd. (abstract of Japan Kokai Tokkyo Koho 80 72,123).
CA 92:198074t (1980) Kageyama et al. (abstract only of Jpan Kokai Tokkyo Koho 79,144,326).
CA 93:71239r (1980) Kageyama et al. (abstract only of Japan Kokai Tokkyo Koho 79,163,530).
CA 93:168840t (1980) Mitsubishi Chem. Ind. Co., Ltd. (abstract only of Japan Kokai Tokkyo Koho 80 94,322).
CA 91:40085s (1979) Nakatomi et al. (abstract only of Japan Tokkyo Koho 79 29,893).
J7 4039-248 (Derwent 81728V, abstract only) Asahi Dow Ltd., Mar. 18, 1969.
Berry, "Tin-Antimony Oxide Catalysts" *Advances in Catalysis*, vol. 30, 97–129 (1981).
Weng et al., "Cooperation Between Phases in Mixed SnSbO Selective Oxidation Catalysts" *New Developments in Selective Oxidation*, 797–806 (1990).
Viswanathan et al., "Some Reflections on Mixed Tin and Antimony Oxide Catalysts" *Surface Technology*, vol. 23, 231–244 (1984).

*Primary Examiner*—Anthony McFarlane
*Assistant Examiner*—P. Achutamurthy
*Attorney, Agent, or Firm*—Robert M. O'Keefe

[57] ABSTRACT

4-Vinylcyclohexene is converted to styrene in the presence of a catalyst comprising tin, antimony, and oxygen. The feed stream to be contacted with the catalyst comprises water, 4-vinylcyclohexene, and oxygen. A ratio of water to 4-vinylcyclohexene above about 12:1, preferably above about 14:1, significantly increases the half-life of the catalyst. The catalyst is prepared by co-precipitating a tin chloride and an antimony chloride followed by calcination of the precipitate at a temperature in the range from 850° C. to 1000° C.

26 Claims, No Drawings

PROCESS FOR THE PRODUCTION OF STYRENE

This application is a continuation-in-part of co-pending application U.S. Ser. No. 07/827,131 filed Jan. 28, 1992, now abandoned.

BACKGROUND OF THE INVENTION

The present invention relates to the gas phase catalytic production of styrene from 4-vinylcyclohexene.

Styrene is an important monomer useful in the production of polymers such as polystyrene. Owing to its important commercial value, effective processes for the production of styrene are highly sought.

An example of a process useful for the production of styrene is disclosed in U.S. Pat. No. 4,165,441. This patent discloses a process for the gas phase oxidative dehydrogenation of 4-vinylcyclohexene in the presence of a catalyst containing tin, antimony, and oxygen. The patent describes the use of water as a component in the feed stream containing 4-vinylcyclohexene. The molar ratio of water to 4-vinylcyclohexene in the feed stream is about 8.5:1. While the patent reports reasonable yields with a variety of catalysts containing tin, antimony, and oxygen, the examples only report data for runs up to a few hours of continuous production of styrene. It is known, however, that under the conditions employed in U.S. Pat. No. 4,165,441, the half-life of the catalyst is quite low. Thus, the process disclosed in U.S. Pat. No. 165,441 results in poor yields after an undesirably short amount of time when the process is run continuously. Similarly, the process disclosed in U.S. Pat. No. 4,165,441 requires frequent stoppage of the process to regenerate the catalyst. Hence, to enable effective commercial use of such a process, it is desirable to increase significantly the half-life of said catalyst and thereby provide a process capable of being used to commercial advantage.

SUMMARY OF INVENTION

This invention, in one respect, is a process for the production of styrene from 4-vinylcyclohexene, comprising contacting a feed stream in the gas phase with a catalyst comprising tin, antimony, and oxygen under conditions sufficient to produce styrene, the feed stream comprising 4-vinylcyclohexene, water, and molecular oxygen, the molar ratio of water to 4-vinylcyclohexene in the feed stream being at least about 12:1 and less than about 30:1, the catalyst having a half-life of at least about 1000 hours, and the catalyst having been prepared by coprecipitating a tin chloride and an antimony chloride to form a precipitate and calcining the precipitate at a temperature in the range from about 850° C. to about 1000° C.

In another respect, this invention is a process for the production of styrene from 4-vinylcyclohexene, comprising contacting a feed stream in the gas phase at a temperature of from about 300° C. to about 500° C. with a catalyst consisting essentially of tin, antimony, oxygen, and a binder under conditions sufficient to produce styrene, the catalyst having a tin/antimony molar ratio in the range from about 7:1 to about the feed stream comprising 4-vinylcyclohexene, water, and oxygen, the molar ratio of water to 4-vinylcyclohexene being at least about 14:1 and less than about 30:1, the catalyst having a half-life of at least about 1000 hours, and the catalyst having been prepared by coprecipitating a tin chloride and an antimony chloride to form a precipitate and calcining the precipitate at a temperature in the range from about 850° C. to about 1000° C.

The half-life of a catalyst containing tin, antimony, and oxygen in a process for the production of styrene from 4-vinylcyclohexene is at least about 1000 hours in a continuous operation when the molar ratio of water to 4-vinylcyclohexene is at least about 12:1. Advantageously this invention provides enhanced half-life of the catalyst employed herein and reduces the frequency at which the catalyst is in need of regeneration.

A catalyst prepared by coprecipitation in accordance with this invention provides higher activity than other methods in processes for the production of styrene from 4-vinylcyclohexene.

DETAILED DESCRIPTION OF THE INVENTION

The catalyst used in this invention comprises tin, antimony, and oxygen. Preferably, the molar ratio of tin to antimony is in the range from about 1:1 to about 20:1, preferably the molar ratio of tin to antimony is in the range from about 1:1 to about 16:1, more preferably the molar ratio of tin to antimony is in the range from about 4:1 to about 16:1, and most preferably the molar ratio of tin to antimony is in the range from about 7:1 to about 11:1. If one or more metals other than tin and antimony are present in the catalyst, the one or more metals can be present in an amount in the range from about 0.01 to about 10 weight percent based on the total weight of the catalyst.

The catalyst can be prepared by a number of techniques such as the mastecation method evaporation-to-dryness method, immersion method, or deposition method.

The tin component of the catalyst can be provided from tin oxides such as stannous oxide and stannic oxide, or pyrolyzed products of organic tin compounds such as tin oxalate or tin acetate. The organic tins may be dissolved in an inorganic acid such as hydrochloric acid and then neutralized with an alkali such as ammonia water. It is also possible to use the products obtained by oxidizing tin metal with nitric acid. Preferably, the tin component of the catalyst is provided from easily hydrolyzable tin halides such as stannous chloride, stannic chloride, etc. Most preferably, the tin component is provided from stannic chloride.

The antimony component of the catalyst can be provided from various sources, for example antimony oxides such as antimony oxide and antimony pentoxide, hydrous antimony oxides such as metaantimonic acid, orthoantimonic acid, and pyroantimonic acid, and the products obtained by oxidizing antimony metals with nitric acid. Preferably, the antimony component is provided from easily hydrolyzable antimony halides such as antimony trichloride and antimony pentachloride. Most preferably, the antimony component is provided from antimony pentachloride.

The catalyst can also contain metals other than tin and antimony. Examples of such metals include iron, molybdenum, manganese, coppery zinc, tellurium, cobalt, and vanadium. These metals can be added to the tin and antimony catalyst from a variety of sources including metal oxides, inorganic salts such as chlorides and nitrates, and organic salts such as acetates and oxalates.

While the catalyst of this invention can contain other metals, it has been found that a catalyst essentially free from added metals other than tin and antimony per-forms better than a catalyst having metals added thereto. A catalyst containing a metal other than tin and antimony is less productive and deactivates faster than a catalyst free of metals other than tin and antimony.

It is preferred that the catalyst be formed by the coprecipitation method from tin and antimony halides. In the coprecipitation method, the tin and antimony halides are thoroughly admixed in appropriate molar proportions. The resulting admixture is then added to stirred water. Typically, the temperature of the water is about 25° C. The pH of the water should be maintained in the range from about 5 to about 10, as by addition of concentrated ammonium hydroxide or other base as the tin and antimony halide admixture is added to the water. Preferably, the pH is maintained in the range from about 7 to about 8.

The admixture can be added to the water at any rate so long as the pH can be maintained in the range from about 5 to about 10. The proportion of the tin and antimony halide admixture to water has a significant bearing on activity of the final catalyst. While proportions in the range from about 0.03 to about 3.0 total moles of admixture to one liter of water is desirable, it is preferred that the proportion be in the range from about 0.07 to about 0.6 total moles of admixture to one liter of water. As the admixture is added to the stirred water, a gel precipitate forms. This gel is collected by conventional techniques such as filtration and then washed. If a metal other than tin and antimony is desired in the final catalyst, a solution containing a salt of said metal can be added to the precipitate. Typically, the solution is added to the precipitate by pouring the solution over the precipitate in a closed vessel to thereby impregnate the precipitate with metal salt solution. The amount of metal salt present in the solution can be varied depending on the amount of metal desired in the final catalyst. Finally, the precipitate, with or without a metal salt solution admixed thereto, is dried.

The dried precipitate, as well as a precipitate or mass recovered from and prepared by a technique other than the coprecipitation method, is next subjected to a calcination treatment to further enhance the catalyst activity. Calcination can be accomplished by calcining the prepared catalyst composition with an oxygen-containing gas, such as airy at a temperature in the range from about 800° C. to about 1200° C. for a time in the range from about 1 to about 24 hours. Preferably, the catalyst is calcined at a temperature in the range from about 850° C. to about 1000° C. for a time in the range from about 1 to about 6 hours. Most preferably, the catalyst is calcined at a temperature in the range from about 900° C. to about 1000° C. for a time in the range from about 1 to about 3 hours. The shape of a catalyst is not critical to the invention, but the catalyst can be formed by conventional methods to produce a final catalyst. For example, the catalyst can be shaped into the form of pellets convenient for use in a fixed bed reaction or can be shaped into granules for use in a fluidized bed reaction.

The catalyst of this invention may be bound with conventional binders such as calcium sulphate, various clays, and refractory oxides, such as silica, alumina, magnesium oxide, zirconium oxide, titanium oxide, and boron oxide. Combinations of two or more binders may be employed such as silica-alumina and silica-magnesia. Typically, the binder is in an amount in the range from about 0.1 to about 50 weight percent of a finished catalyst. The weight percent of binder varies depending on the particular binder employed.

The process of this invention for the production of styrene can be carried out in any known manner used for gas phase processes and the catalyst can be used either as a fixed bed, a fluidized bed, or a moving bed. Likewise, multiple beds and multiple reactant injection sites can be employed. The temperature in this process is usually from about 250° C. to about 600° C., preferably from about 300° C. to about 500° C. This process can be performed under sub-atmospheric, atmospheric, or super-atmospheric pressures.

For purposes of this invention, "gas hourly space velocity" ("GHSV") is defined as the value of the volume of feed stream which passes per hour per unit volume over the catalyst. In case of using the catalyst of this invention in a process for the production of styrene from 4-vinylcyclohexene, GHSV is in the range from about 50,000 $hr^{-1}$ to about 100 $hr^{-1}$, preferably about 5,000 $hr^{-1}$ to about 1,000 $hr^{-1}$.

The feed stream of this invention comprises 4-vinylcyclohexene, oxygen, and water. The 4-vinylcyclohexene used in this process need not be high in purity and may contain other cyclic or chain hydrocarbons. The molar ratio of oxygen to 4-vinylcyclohexene in the feed stream is in the range from about 0.5:1 to about 10:1, preferably in the range from about 0.5:1 to about 3:1. In addition, the feed stream can further comprise a diluent gas which is essentially inert to the reaction of this invention. An example of a diluent gas is nitrogen.

It is critical to the present invention that the amount of water in the feed stream be maintained such that the molar ratio of water to 4-vinylcyclohexene is at least about 12:1, most preferably the molar ratio of water to 4-vinylcyclohexene is at least about 14:1. The molar ratio of water to 4-vinylcyclohexene is preferably less than about 50:1, more preferably less than about 30:1. When the molar ratio of water to 4-vinylcyclohexene is at least about 12:1 in a process to produce styrene from 4-vinylcyclohexene in the presence of a catalyst used in this invention and under conditions sufficient to produce styrene, the half-life of the catalyst is at least about 1000 hours, preferably at least about 1500 hours, more preferably at least about 2000 hours, even more preferably at least about 2500 hours. It is understood, however, that half-life will vary depending on reaction conditions such as temperature. For purposes of this invention, "half-life" is defined as the time required for conversion to be reduced by half under steady state conditions (constant feed rates, reaction temperature, and pressure). For example, if the conversion is 90 percent initially, the half-life is obtained when the conversion drops to 45 percent. Half-life can be estimated by extrapolation of the data as recognized by skilled artisans.

The catalyst can be regenerated as needed by methods known to those skilled in the art. For examples, the catalyst can be regenerated by passing an oxygen-containing gas, such as air, over the catalyst at elevated temperatures.

For purposes of this invention, "conversion" is defined as the mole percentage of the moles of reactant, such as 4-vinylcyclohexene, lost from the feed stream as a result of reaction divided by mole percentage of reactant in the feed times 100. The conversion can vary widely depending upon the reactants, the form of the catalyst, and the process conditions such as temperature, pressure, flow rate, and catalyst residence time. Within the preferred gas hourly space velocity range, as the space velocity increases the conversion generally decreases. Typically, the conversion of 4-vinylcyclohexene is at least about 30 mole percent. Preferably, the conversion is at least about 40 mole percent, more preferably at least about 50 mole percent, and most preferably at least about 60 mole percent. The styrene formed from the process can be separated from feed stream components by well known methods such as by distillation. The 4-vinylcyclohexene recovered after the first pass conversion can be recycled into the feed stream. Hence, by recycling unconverted 4-vinylcyclohexene, the conversion can approach 99–100 percent in a commercial operation.

For the purposes of this invention, "selectivity" is defined as the mole percentage of converted 4-vinylcyclohexene that forms styrene. Typically, selectivities also vary widely depending upon the reactants, the form of the catalyst, and the process conditions. Within the preferred space velocity range, as the space velocity increases the selectivity for styrene generally increases. Typically, the selectivity to styrene is at least about 80 mole percent. Preferably, the selectivity to styrene is at least about 85 mole percent.

The concept of simultaneous high conversion and high selectivity can be conveniently expressed in terms of yield. For the purposes of this invention, the term "yield" refers to the numerical product of the single-pass conversion and selectivity. For example, a process according to the present invention operating at a conversion of 90 mole percent, and a selectivity to styrene of 90 mole percent, would have a styrene yield of 81 mole percent. Typically, the yield of styrene achieved in the process of this invention is at least about 30 mole percent. Preferably, the yield of styrene achieved in the process of this invention is at least about 50 mole percent.

The rate at which a desired product is produced in the process of this invention can be expressed in the concept of productivity. The "productivity" is defined as the weight of styrene formed divided by the volume of catalyst per hour. Preferably, the productivity of styrene in the process of this invention is at least about 5 pounds per cubic foot per hour (0.08 grams per cubic centimeter per hour), more preferably, at least about 10 pounds per cubic foot per hour (0.16 grams per cubic centimeter per hour), and most preferably, at least about 15 pounds per cubic foot per hour (0.24 grams per cubic centimeter per hour).

The following examples are given to illustrate the process of this invention and should not be construed as limiting its scope. All percentages in the examples are mole percent unless otherwise indicated.

Preparation of Catalysts (a) A series of catalysts, A–G, were prepared according to the following general procedure. For each catalyst, the moles of tin and antimony were adjusted according to the tin/antimony molar ratio desired. The tin/antimony molar ratios, as well as results of Examples 1–10, described hereinbelow, are reported in Table I.

Antimony pentachloride (8.5 ml, 0.0664 mole) and stannic chloride (68.5 ml, 0.585 mole) were thoroughly mixed. The admixture was added dropwise to 4 liters of rapidly mixed, 25° C. deionized water maintained at a constant pH of 7.2 by adding concentrated ammonium hydroxide. The gel precipitate formed was then filtered, washed, dried, and calcined at 950° C. in a flowing stream of air for two hours to form the final catalyst. The catalyst had a tin/antimony molar ratio of about 9:1.

(b) The general procedure of (a) was followed to form catalyst H except 900 ml of deionized water was used instead of 4 liters.

(c) The general procedure of (a) was followed to form catalyst I except the calcination temperature was 750° C. instead of 950° C.

(d) Catalyst J was prepared by adding 47.4 g of tin metal and 6.02 g of antimony metal to 400 ml of concentrated nitric acid (Sn/Sb mole ratio of 8.1:1). After heating the solution for 1 hour at 80° C., the excess liquid was removed. The catalyst was placed in a quartz tube and was calcined in air at 950° C. for two hours.

(e) Catalyst K having a tin/antimony molar ratio of 9:1 was prepared via precipitation. A mixture was made from antimony pentachloride (4.25 ml 0.033 moles) and tin tetrachloride (34.25 ml, 0.29 moles). This mixture was added dropwise to 2 liters of rapidly mixed deionized water maintained at a constant pH of 7.2 by adding concentrated ammonium hydroxide. The gel precipitate formed was then filtered and was washed with deionized water. Before drying an aqueous solution containing 1.28 gram of cupric chloride dihydrate was added. The catalyst was then dried and calcined at 950° C. in a flowing stream of air for two hours. The finished catalyst had a tin/antimony molar ratio of about 9:1 and contained about 1.5 weight percent copper.

(f) The procedure of (e) was repeated to form Catalyst L except 1.49 gram of ferrous chloride tetrahydrate was substituted for cupric chloride dihydrate. The final catalyst contained 1.5 weight percent iron.

(g) Catalyst M having a tin/antimony molar ratio of 9:1 was prepared via precipitation. A mixture was made from antimony pentachloride (4.16 ml 0.032 moles) and tin tetrachloride (34.25 ml, 0.29 moles). This mixture was added dropwise to 2 liters of rapidly mixed deionized water maintained at a constant pH of 7.2 by adding concentrated ammonium hydroxide. The gel precipitate formed was then filtered and washed with deionized water. Before drying, an aqueous solution containing 1.9 gram of calcium sulfate was added. The catalyst was then dried and calcined at 950° C. in a flowing stream of air for two hours. The finished catalyst had a tin/antimony molar ratio of about 9:1 and contained about 1 weight percent calcium.

Examples 1–12

Conversion of 4-Vinylcyclohexene to Styrene

The following general procedure was repeated for Examples 1–12. The results of each run, corresponding to catalysts A–D and F–M, are reported in Table I. In Examples 1–12, standard feed conditions were defined as: 4-vinylcyclohexene ("VCH") feed rate of 3 ml/hr; water feed rate of 6 ml/hr, and a feed rate of 187 ml/minute of a gaseous mixture having 93 percent nitrogen and 7 percent oxygen. The standard feed had a water/VCH/oxygen/nitrogen molar ratio of 14.4:1:1.506:19.9. The standard feed was flowed over 10 ml of catalyst in a fixed bed reactor. The reported conversions, selectivities, and yields were those obtained at the indicated times after start of the runs.

TABLE I

| Example | Catalyst | Sn:Sb Molar Ratio | Temp. (°C.) | Hours of Continuous Operation | VCH Conversion | Selectivity to Styrene | Yield (%) | Styrene Productivity (g/cc-hr) |
|---|---|---|---|---|---|---|---|---|
| 1 (a) | A | 1:3 | 398 | 8 | 70 | 89 | 62 | 0.149 |
| (b) | | | 377 | 5 | 67 | 84 | 56 | 0.135 |
| 2 (a) | B | 1:1 | 378 | 46 | 82 | 87 | 71 | 0.171 |
| (b) | | | 396 | 12 | 90 | 90 | 81 | 0.194 |
| 3 | C | 3:1 | 400 | 24 | 85 | 83 | 71 | 0.171 |
| 4 (a) | D | 4.9:1 | 399 | 21 | 90 | 83 | 75 | 0.180 |
| (b) | | | 382 | 29 | 92 | 73 | 67 | 0.161 |
| 5 | F | 9:1 | 380 | 24 | 98 | 93 | 91 | 0.218 |
| 6 (a) | G | 19:1 | 398 | 20 | 56 | 84 | 47 | 0.113 |
| (b) | | | 376 | 32 | 38 | 85 | 32 | 0.077 |
| 7 | H | 9:1 | 398 | 24 | 60 | 84 | 50 | 0.120 |
| 8 | I | 9:1 | 380 | 37 | 65 | 85 | 55 | 0.132 |
| 9 | J | 8.1:1 | 400 | 2 | 93.3 | 92.6 | 86.4 | 0.208 |
| | | | | 25 | 92.5 | 92.7 | 85.7 | 0.206 |
| | | | | 46 | 91.8 | 92.5 | 84.9 | 0.204 |
| | | | | 64 | 91.1 | 92.9 | 84.7 | 0.204 |
| | | | | 96 | 89.9 | 92.5 | 83.2 | 0.200 |
| | | | | 101 | 89.4 | 92.6 | 82.8 | 0.199 |
| 10 | K | 9:1 with 1.6 percent copper | 399 | 6 | 90.6 | 90.7 | 82.2 | 0.199 |
| | | | | 24 | 90.2 | 90.3 | 81.5 | 0.196 |
| | | | | 43.5 | 89.3 | 90.1 | 80.5 | 0.193 |
| | | | | 61 | 88.8 | 90.1 | 80.0 | 0.192 |
| | | | | 96 | 87.9 | 89.8 | 79.0 | 0.190 |
| | | | | 99 | 87.8 | 89.8 | 78.9 | 0.190 |
| 11 | L | 9:1 with 1.5 percent iron | 380 | 1.0 | 97.2 | 96.8 | 94.1 | 0.226 |
| | | | | 17.0 | 95.8 | 94.2 | 90.3 | 0.217 |
| | | | | 25.0 | 92.1 | 92.3 | 85.0 | 0.204 |
| | | | | 44.0 | 83.6 | 91.4 | 76.4 | 0.184 |
| | | | | 68.0 | 73.9 | 88.7 | 65.5 | 0.157 |
| | | | | 73.0 | 72.7 | 88.4 | 64.3 | 0.154 |
| 12 | M | 9:1 with 1 percent calcium sulphate binder | 399 | 3.0 | 61 | 89.2 | 56 | 0.134 |
| | | | | 20.5 | 60 | 90.5 | 56 | 0.134 |
| | | | | 25.5 | 60 | 90.5 | 56 | 0.134 |

It can bee seen in Table I the catalyst prepared by coprecipitation in Example 5, catalyst F, exhibited superior activity compared with the catalyst of Example 9, catalyst J, catalyst J having been prepared by the method noted above wherein antimony and tin metals are place in nitric acid followed by recovery and calcination at 950° C. Thus it is seen that catalyst J required a temperature of 400° C. to achieve a productivity of about 0.2, whereas catalyst F (calcined at 950° C., having a slightly higher Sn:Sb mole ratio) produces a higher productivity of 0.218 at 380° C. Thus it is readily seen that catalysts prepared by coprecipitation produce superior productivity in the process.

EXAMPLE 13-14

Conversion of 4-Vinylcyclohexene to Styrene

The procedure of Examples 1-12 was repeated except the flow rates were doubled: VCH, 6 ml/hr; water, 12 ml/hr; 93 percent nitrogen and 7 percent oxygen, 375 ml/min. The water/VCH molar ratio is 14.4:1. The results are reported in Table II.

TABLE II

| Example | Catalyst | Sn:Sb Molar Ratio | Temp. (°C.) | Hours of Continuous Operation | VCH Conversion | Selectivity to Styrene | Yield (%) | Styrene Productivity (g/cc-hr) |
|---|---|---|---|---|---|---|---|---|
| 13 | E | 8.5:1 | 400 | 3 | 96.9 | 93.8 | 91 | 0.437 |
| | | | | 31.5 | 96.5 | 94.3 | 91 | 0.437 |
| | | | | 75.5 | 95.2 | 94.0 | 90 | 0.430 |
| | | | | 121 | 94.3 | 94.0 | 90 | 0.430 |
| | | | | 145 | 94.2 | 94.5 | 89 | 0.428 |
| | | | | 169 | 94.1 | 93.8 | 88 | 0.424 |
| | | | | 176 | 94.0 | 93.6 | 88 | 0.423 |
| 14 | F | 9:1 | 400 | 24 | 97.1 | 93.7 | 91 | 0.437 |
| | | | | 31.5 | 96.6 | 94.0 | 91 | 0.437 |
| | | | | 96.0 | 96.2 | 93.9 | 90 | 0.434 |
| | | | | 121.0 | 95.4 | 94.0 | 90 | 0.431 |
| | | | | 145.0 | 94.2 | 94.0 | 89 | 0.426 |
| | | | | 176.0 | 94.0 | 93.6 | 88 | 0.423 |
| | | | | 200.0 | 93.2 | 93.6 | 87 | 0.414 |
| | | | | 268.0 | 92.8 | 93.5 | 87 | 0.417 |
| | | | | 300.0 | 92.5 | 93.4 | 86 | 0.415 |

In Example 13, the half-life of the catalyst was estimated to be 2900 hours by extrapolation of the data points. In Example 14, the half-life was estimated to be 2800 hours by extrapolation of the data points.

Comparative Experiment 1 (Not an embodiment of the invention)

The general procedure of Example 13 using catalyst E was repeated except the water feed rate was 6 ml/hour; thus, the water/VCH molar ratio was 7.2:1. The following data was obtained.

| Time (Hours) | Conversion (%) | Yield Styrene (%) | Styrene Productivity (g/cc-hr) |
|---|---|---|---|
| 4 | 97.2 | 91.4 | 0.439 |
| 23 | 96.6 | 90.3 | 0.434 |
| 28 | 95.3 | 89.7 | 0.431 |
| 55 | 94.0 | 88.0 | 0.423 |
| 95 | 87.6 | 80.6 | 0.387 |
| 100 | 86.2 | 79.3 | 0.318 |
| 119 | 82.3 | 74.7 | 0.354 |
| 124 | 81.4 | 73.9 | 0.355 |
| 143 | 76.8 | 68.6 | 0.329 |
| 148 | 76.6 | 67.9 | 0.326 |
| 172 | 71.5 | 62.7 | 0.301 |

The half-life of this catalyst, when the water/VCH molar ratio was 7.2:1 was estimated to be about 215 hours.

Comparative Experiment 2 (Not an embodiment of the invention)

The procedure of Example 9 using catalyst J was repeated except the water feed rate was 6 ml/hour; thus, the water/VCH molar ratio was 7.2:1. The following data was obtained.

| Time (Hours) | Conversion (%) | Yield Styrene (%) | Styrene Productivity (g/cc-hr) |
|---|---|---|---|
| 2.0 | 95.8 | 90.6 | 0.436 |
| 8.0 | 94.4 | 88.7 | 0.426 |
| 24.0 | 91.7 | 85.3 | 0.410 |
| 48.0 | 86.3 | 79.7 | 0.383 |
| 56.0 | 83.8 | 76.5 | 0.368 |
| 75.0 | 79.1 | 70.9 | 0.341 |
| 106.0 | 73.1 | 64.1 | 0.308 |

It can be seen from Comparative Experiments 1 and 2 that the molar ratio of water to VCH in the feed stream had a dramatic effect on the half-life of the catalyst. In Examples 9 and 13 the water/VCH mole ratio was 14.4 in the feed stream. In Comparative Experiments 1 and 2, however, the water/VCH mole ratio was 7.2. In both comparative experiments 1 and 2, conversion and yield had dropped significantly as compared to Examples 9 and 13.

Comparative Experiment 3 (Not an embodiment of the invention)

The procedure of Example 10 using catalyst K was repeated except the water feed rate was 6 ml/hour; thus, the water/VCH molar ratio was 7.2: 1. The following data was obtained.

| Time (Hours) | Conversion (%) | Yield Styrene (%) | Styrene Productivity (g/cc-hr) |
|---|---|---|---|
| 5 | 83.2 | 73.2 | 0.352 |
| 26 | 79.6 | 69.0 | 0.331 |
| 31 | 79.3 | 68.8 | 0.331 |
| 50.5 | 79.2 | 68.4 | 0.329 |
| 55.5 | 78.9 | 68.0 | 0.327 |
| 74.5 | 78.6 | 67.6 | 0.325 |
| 81 | 78.5 | 67.5 | 0.324 |

It can be seen from Comparative Experiment 3 when compared to Example 10, that the increase of water in the feed stream also increased half-life for a metal-doped catalyst.

EXAMPLE 15

The procedure of Example 14 was repeated using catalyst F at 400° C. with the proviso that the amount of water was varied to correspond with those shown in Table III below. In Table III the phrase "Styrene Produced" represents the integrated amount of styrene produced in arbitrary units, over a 175 hour time period. Data with an asterisk were from short runs and were extrapolated to 175 hours assuming no catalyst deactivation.

TABLE III

| Water/VCH mole ratio | Styrene Produced |
|---|---|
| 2.2 | 83* |
| 7.2 | 151 |
| 8.6 | 154 |
| 12.0 | 160 |
| 14.4 | 167 |
| 21.6 | 162* |
| 28.8 | 156* |
| 36.1 | 150* |
| 72.1 | 122* |
| 144.3 | 79* |

It can be seen from the data in Table III that the water/VCH mole ratio had an important impact on the amount of styrene produced in a given time period. A maximum was observed in the range from 12.0 to approximately 30.0, inclusive. Below 12.0 and above 28.8 the styrene produced decreases.

EXAMPLE 16

The procedure of Example 14 was repeated except the feed rate over the catalyst was increased such that the VCH feed rate was 9.6 mL/hr, the water feed rate was 19.2 mL/hr, and the feed rate of a nitrogen/oxygen mixture (93% nitrogen and 7% oxygen) was 600 cc/min. Under these conditions, the conversion decreased to 85.1 mole percent; selectivity to styrene is 92.2 mole percent; which corresponds to a styrene productivity of 0.603 grams per cubic centimeter per hour.

Comparative Experiment 4 (Not an embodiment of the invention)

A catalyst was prepared by the slow addition of 47.4 grams of tin metal and 5.4 grams of antimony metal to 500 mL of rapidly stirred concentrated nitric acid. The mixture was heated to 90° C. with continual stirring to completely digest the metal. The mixture was then dried at 100° C. and then calcined, in flowing air, by heating at 2.5° C./minute from room temperature to 950° C. and then holding isothermally at 950° C. for two hours. After cooling a 10.0 cc sample of this catalyst (tin/antimony mole ratio of 9:1) was tested under identical conditions as for Example 14. The results were as follows.

| Time (Hours) | Conversion (%) | Yield Styrene (%) | Styrene Productivity (g/cc-hr) |
|---|---|---|---|
| 3 | 88.4 | 82.8 | 0.398 |
| 21 | 86.1 | 80.3 | 0.386 |
| 27 | 85.7 | 80.1 | 0.385 |
| 45 | 83.9 | 78.1 | 0.375 |
| 48 | 83.8 | 77.8 | 0.374 |
| 62 | 83.1 | 77.0 | 0.370 |

When a comparison is made between the results of Example 14 and Comparative Experiment 4, it is seen that the catalyst prepared by coprecipitation is superior to the catalyst prepared in Comparative Experiment 4 (the mole ratio of antimony to tin the calcination temperature, and the conditions being the same in Example 14 and Comparative Experiment 4). For instance, at 21 hours and 27 hours in Comparative Experiment 4 the styrene yield is 80.3 percent and 80.1 percent, respectively, whereas in Example 14 the yield was over 10 percent greater being 91 percent at 24 hours. This data shows a catalyst prepared by coprecipitation is superior to a catalyst prepared by the procedure in Comparative Experiment 4.

In addition, another experiment was performed using the catalyst of Comparative Experiment 4 using the same procedure above to make styrene except that the flow rates were changed from initial gas space velocity of 3820 sec$^{-1}$ to lower values until a conversion was reached that was the same as in Example 14 at 200 hours wherein the productivity was 0.419 g/cc-hr, this lower rate being 2290 sec$^{-1}$ (VCH flow rate of 3.6 mL/hr, water flow rate of 7.2 mL/hr and gaseous 7 percent oxygen in nitrogen of 224 cc/minute). Thus, at a space velocity of 2290 sec$^{-1}$, the catalyst of Comparative Experiment 4 produced a 93.3 percent VCH conversion and a productivity of 0.256 g/cc-hr. This difference in space velocities is significant in that the ratio of space velocities (3820 sec$^{-1}$/2290 sec$^{-1}$=1.668) shows the catalyst of Example 14 to be at least 67 percent more active than the catalyst prepared according to Comparative Experiment 4 because the catalyst of Example 14 achieves the same conversion as the catalyst of Comparative Experiment 4 except that the catalyst of Example 14 can do so at a much higher space velocity. Likewise, the productivity in Example 14 was 0.419 g/cc-hr whereas the catalyst of Comparative Experiment 4 at a gas hourly space velocity of 2290 sec$^{-1}$ was less being 0.256 g/cc-hr.

What is claimed is:

1. A process for the production of styrene from 4-vinylcyclohexene, comprising contacting a feed stream in the gas phase with a catalyst comprising tin, antimony, and oxygen under conditions sufficient to produce styrene, the feed stream comprising 4-vinylcyclohexene, water, and molecular oxygen, the molar ratio of water to 4-vinylcyclohexene in the feed stream being at least about 12:1 and less than about 30:1, the catalyst having a half-life of at least about 1000 hours, and the catalyst having been prepared by coprecipitating a tin halide and an antimony halide to form a precipitate and calcining the precipitate at a temperature in the range from about 850° C. to about 1000° C.

2. The process of claim 1 wherein the molar ratio of water to 4-vinylcyclohexene in the feed stream is at least about 4:1.

3. The process of claim 1 wherein the tin halide is stannic chloride and the antimony halide is antimony pentachloride.

4. The process of claim 1 wherein the temperature at which the feed stream is contacted with the catalyst is in the range from about 300° C. to about 500° C.

5. The process of claim 1 wherein the catalyst is calcined at a temperature in the range from about 900° C. to about 1000° C. prior to use in the process.

6. The process of claim 1 wherein the catalyst has a atomic ratio of tin to antimony in the range from about 1:1 to about 20:1.

7. The process of claim 1 wherein the catalyst has a atomic ratio of tin to antimony in the range from about 1:1 to about 16:1.

8. The process of claim 1 wherein the catalyst has a atomic ratio of tin to antimony in the range from about 5:1 to about 16:1.

9. The process of claim 1 wherein the catalyst has a atomic ratio of tin to antimony in the range from about 7:1 to about 11:1.

10. The process of claim 1 wherein the molar ratio of oxygen to 4-vinylcyclohexene is in the range from about 0.5:1 to about 3:1.

11. The process of claim 1 wherein the catalyst has a half-life of at least about 1500 hours.

12. The process of claim 1 wherein the catalyst has a half-life of at least about 2000 hours.

13. The process of claim 1 wherein the catalyst has a half-life of at least about 2500 hours.

14. The process of claim 1 wherein the feed stream further comprises a diluent.

15. The process of claim 1 wherein the molar ratio of water to 4-vinylcyclohexene is at least about 14:1.

16. The process of claim 8 wherein the catalyst consists essentially of tin antimony, oxygen, and a binder.

17. The process of claim 9 wherein the catalyst consists of tin antimony, oxygen, and a binder.

18. A process for the production of styrene from 4-vinylcyclohexene, comprising contacting a feed stream in the gas phase at a temperature of from about 300° C. to about 500° C. with a catalyst consisting essentially of tin, antimony, oxygen, and a binder under conditions sufficient to produce styrene, the catalyst having a tin/antimony atomic ratio in the range from about 7:1 to about 11:1, the feed stream comprising 4-vinylcyclohexene, water, and oxygen, the molar ratio of water to 4-vinylcyclohexene being at least about 14:1 and less than about 30:1, the catalyst having a half-life of at least about 1000 hours, and the catalyst having been prepared by coprecipitating a tin halide and an antimony halide to form a precipitate and calcining the precipitate at a temperature in the range from about 850° C. to about 1000° C.

19. The process of claim 18 wherein the tin halide is stannic chloride and the antimony halide is antimony pentachloride.

20. The process of claim 18 wherein the catalyst was calcined at a temperature of from about 900° C. to about 1000° C. prior to the process.

21. The process of claim 18 wherein the binder is selected from the group consisting of calcium sulphate, silicas alumina, magnesium oxide, boron oxide, titanium oxides zirconium oxide, and combinations thereof.

22. The process of claim 18 wherein the molar ratio of oxygen has 4-vinylcyclohexene is in the range from about 0.5:1 to about 3:1.

23. The process of claim 18 wherein the catalyst has a half-life of at least about 1500 hours.

24. The process of claim 18 wherein the catalyst has a half-life of at least about 2000 hours.

25. The process of claim 18 wherein the catalyst has a lifetime of at least about 2500 hours.

26. The process of claim 18 wherein the feed stream further comprises a diluent.

* * * * *

UNITED STATES PATENT AND TRADEMARK OFFICE
CERTIFICATE OF CORRECTION

PATENT NO  : 5,336,822

DATED      : August 9, 1994

INVENTOR(S) : Dennis A. Hucul

It is certified that error appears in the above-identified patent and that said Letters Patent are hereby corrected as shown below:

Col. 11, Line 3 of Claim 2, "4:1" should read -- 14:1 --.

Col. 12, Line 2 of Claim 16, "tin antimony," should read -- tin, antimony, --.

Col. 12, Line 2 of Claim 17, "tin antimony," should read -- tin, antimony, --.

Col. 12, Line 3 of Claim 21, "silicas" should read -- silica, --.

Col. 12, Line 4 of Claim 21, "oxides" should read -- oxide, --.

Signed and Sealed this

Eighteenth Day of April, 2000

Q. TODD DICKINSON

*Attest:*

*Attesting Officer*   *Director of Patents and Trademarks*